United States Patent [19]

Fisher et al.

[11] 4,200,581

[45] Apr. 29, 1980

[54] ALKYL DERIVATIVES OF C-076 COMPOUNDS

[75] Inventors: Michael H. Fisher, Ringoes; Aino Lusi, Rahway; Richard L. Tolman, Berkeley Heights, all of N.J.

[73] Assignee: Merck & Co., Inc., Rahway, N.J.

[21] Appl. No.: 930,845

[22] Filed: Aug. 4, 1978

[51] Int. Cl.$^2$ .................. C07H 17/08; C07D 493/22; A61K 31/71; A61K 31/365
[52] U.S. Cl. ................................... 424/180; 424/279; 260/343,41; 536/17 A
[58] Field of Search .................. 260/343.41; 536/17; 424/180, 279

[56] References Cited

U.S. PATENT DOCUMENTS 3,950,360   4/1976   Aoki et al. ................. 260/343.41

FOREIGN PATENT DOCUMENTS 27170407   10/1977   Fed. Rep. of Germany .

OTHER PUBLICATIONS

Mishima et al. Tetrahedron letters 10, pp. 711–714, 1975.
Journal of Antibiotics 29(6) Jun. 1976, pp. 76–34 to 76–42 and pp. 76–14 to 76–16.

*Primary Examiner*—Henry R. Jiles
*Assistant Examiner*—Jane T. Fan
*Attorney, Agent, or Firm*—David L. Rose; Harry E. Westlake

[57] ABSTRACT

Derivatives of C-076, a series of macrolides are described, in which the substituents are hydrocarbon groups. The hydrocarbon groups generally are alkyl groups which may be straight or branched and may optionally be substituted with phenyl. The substituted C-076 compounds are prepared by various procedures depending upon the position of the reaction site, and the particular C-076 compound being substituted. The compounds have profound anthelmintic, insecticidal, ectoparasiticidal and acaracidal activity and compositions for such uses are also disclosed.

24 Claims, No Drawings

ALKYL DERIVATIVES OF C-076 COMPOUNDS

BACKGROUND OF THE INVENTION

The term C-076 is used to describe a series of compounds isolated from the fermentation broth of a C-076 producting strain of *Streptomyces avermitilis*. The morphological characteristics of the culture are completely described in copending U.S. Patent Application Ser. No. 772,601. The C-076 compounds are a series of macrolide with hydroxy substituents capable of being substituted with hydrocarbon substituents. Some of the C-076 compounds have more then one hydroxy group which may be so substituted, and procedures have been developed for the selective substitution at the various positions. The hydrocarbon substituted compounds thus produced have profound anthelmintic, insecticidal, ectoparasiticidal and acaricidal activity.

SUMMARY OF THE INVENTION

The C-076 series of compounds have the following structure:

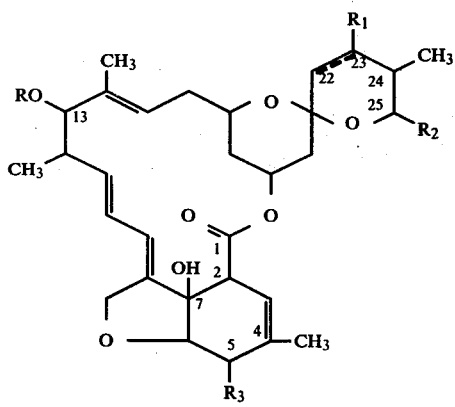

wherein R is the α-L-oleandrosyl-α-L-oleandrosyl group of the structure:

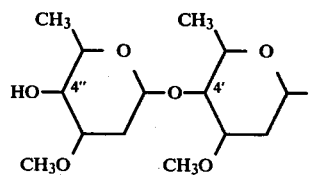

and wherein the broken line between $C_{22}$ and $C_{23}$ indicates a single or a double bond; $R_1$ is hydroxy and is present only when said broken line indicates a single bond;

$R_2$ is iso-propyl or sec-butyl; and $R_3$ is methoxy or hydroxy.

There are eight different C-076 compounds and they are given the designations A1a, A1b, A2a, A2b, B1a, B1b, B2a, B2b based upon the structure of the individual compounds.

In the foregoing structural formula, the individual C-076 compounds are as set forth below.

|     | $R_1$       | $R_2$     | $R_3$   |
|-----|-------------|-----------|---------|
| A1a | Double bond | sec-butyl | —OCH₃   |
| A1b | Double bond | iso-propyl| —OCH₃   |

-continued

|     | $R_1$       | $R_2$     | $R_3$   |
|-----|-------------|-----------|---------|
| A2a | —OH         | sec-butyl | —OCH₃   |
| A2b | —OH         | iso-propyl| —OCH₃   |
| B1a | Double bond | sec-butyl | —OH     |
| B1b | Double bond | iso-propyl| —OH     |
| B2a | —OH         | sec-butyl | —OH     |
| B2b | —OH         | iso-propyl| —OH     |

Based on taxonomic studies, the micro-organisms capable of producing these C-076 compounds are of a new species of the genus Streptomyces, which has been named *Streptomyces avermitilis*. One such culture, isolated from soil is designated MA-4680 in the culture collection of Merck & Co., Inc., Rahway, New Jersey. A C-076 producing sample of this culture has been deposited in the permanent culture collection of the Fermentation Section of the Northern Utilization Research Branch, U.S. Department of Agriculture at Peoria, Illinois, and has been assigned the acession number NRRL 8165. A sample of NRRL 8165 has also been deposited, with restriction as to availability, in the permanent culture collection of the American Type Culture Collection at 12301 Parklawn Drive, Rockville, Maryland 20852, and has been assigned the accession number ATCC 31,267.

The above microorganism is illustrative of a strain of *Streptomyces avermitilis* which can be employed in the production of the C-076 compounds. However, such description also embraces mutants of the above described microorganism. For example, those C-076 producing mutants which are obtained by natural selection or those produced by mutating agents including X-ray irradiation, ultraviolet irradiation, nitrogen mustard or like treatments are also included within the ambit of this invention.

One example of such an organism is a strain of *Streptomyces avermitilis* MA 4848 which was isolated after irradiation with ultraviolet light of *Streptomyces avermitilis* MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

As is readily seen, all of the C-076 compounds have hydroxy groups at the 7-position and the 4''-position of the carbohydrate side chain and hydroxy groups are also found at the 5 and 23 positions. Thus all of the compounds have at least two hydroxy groups capable of substitution.

The carbohydrate side chain may also be hydrolyzed to remove one or both of the α-L-oleandrosyl groups. In this case there would remain an acylatable hydroxy group at the 4' or 13-position with the removal of a single α-L-oleandrosyl group (monosaccharide) or both α-L-oleandrosyl groups (aglycone) respectively.

The monosaccharide and aglycone derivatives are prepared by the treatment of the parent C-076 compound with acid. The outer α-L-oleandrose group is more easily removed than the α-L-oleandrose group directly bonded to the C-076 aglycone thus facilitating the separate preparation of the monosaccharide and aglycone without significant contamination with the other reaction product.

The process employed for the removal of the C-076 carbohydrate group or groups is to put the C-076 starting material in solution in a mixture of from 0.01 to 10% acid in a nonnucleophilic water miscible solvent such as dioxane, tetrahydrofuran, dimethoxyethane, dimethylformamide, bis-2-methoxyethyl ether and the like, and from 0.1 to 20% water. The mixture is stirred for from 6 to 24 hours at room temperature to complete the reaction. Acids such as sulfuric, hydrochloric, hydrobromic, phosphoric, trifluoroacetic and trifluorosulfonic are acceptable. Sulfuric acid is preferred.

When lower acid concentrations such as from 0.01 to 0.1% are employed the monosaccharide is predominantly prepared. When higher concentrations of acid are employed, such as in the range of 1 to 10%, the aglycone is predominantly prepared. Intermediate concentrations of acid will tend to prepare mixtures of monosaccharide and aglycone which are generally separable using chromatographic techniques.

The monosaccharide may also be prepared by stirring the C-076 precursor for from 6 to 24 hours at room temperature in 1% sulfuric acid in isopropanol. In addition the aglycone can be prepared by stirring the C-076 precursor for from 6 to 24 hours at room temperature in 1% sulfuric acid in methanol. The other acids listed above may also be employed in this process. This process is preferred for use with the 2- series of C-076 compounds, since some addition may be observed to the 22,23 double bond of the series of C-076 compounds with a 22,23 unsaturation. The desired monosaccharide or aglycone are isolated and purified using techniques known to those skilled in the art.

The compounds of this invention are realized in the following structural formula:

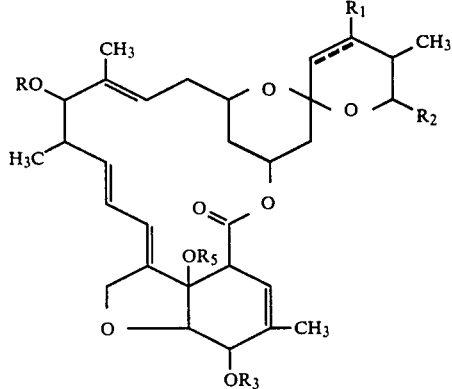

wherein the broken line indicates a single or a double bond;

$R_1$ is hydroxy, loweralkanoyloxy or a hydrocarbonoxy and is present only when said broken line indicates a single bond;

$R_2$ is iso-propyl or sec-butyl;

$R_3$ is hydrogen, methyl, loweralkanoyl or a hydrocarbon; R is hydrogen, loweralkanoyl a hydrocarbon, or

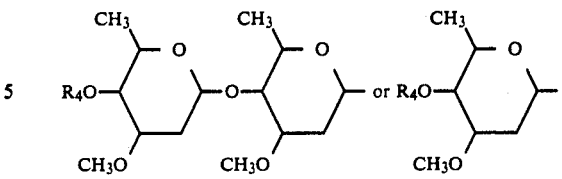

where $R_4$ is hydrogen, loweralkanoyl or a hydrocarbon, and $R_5$ is hydrogen or methyl; and said hydrocarbonoxy group of $R_1$ is an alkoxy of from 1 to 10 carbon atoms or an alkoxy of from 1 to 10 carbon atoms substituted by phenyl and said hydrocarbon group in R, and $R_4$ is an alkyl of from 1 to 10 carbon atoms or an alkyl of from 1 to 10 carbon atoms substituted by phenyl; and said hydrocarbon group in $R_3$ is an alkyl of from 2 to 10 carbon atoms or an alkyl of from 1 to 10 carbon atoms substituted by phenyl; provided that at least one of the R, $R_1$, $R_3$, or $R_4$ groups is or contains a hydrocarbon group or $R_5$ is methyl.

The foregoing alkyl groups and substituted alkyl groups may be either straight or branched chain and are represented by methyl, ethyl, propyl, isopropyl, butyl, isobutyl, sec-butyl, tert-butyl, pentyl, neo-pentyl, hexyl, heptyl, octyl, nonyl, decyl, and the like.

The term "loweralkanoyl" is intended to include those alkanoyl groups containing from 2 to 6 carbon atoms in a straight or branched configuration. Exemplary of such groups are acetyl, propionyl, butyryl, pentanoyl, pivaloyl, hexanoyl, and the like.

The preferred compounds of this invention are realized in the above structural formula when the broken line indicates a single or a double bond;

$R_1$ is hydroxy or a hydrocarbonoxy and is present only when the broken line indicates a single bond;

$R_2$ is iso-propyl or sec-butyl;

$R_3$ is hydrogen, methyl or a hydrocarbon;

R is hydrogen, a hydrocarbon or

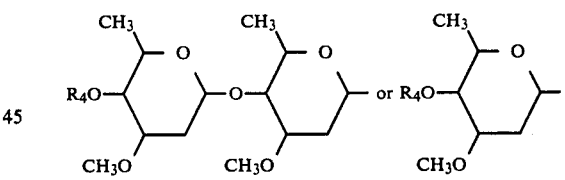

wherein $R_4$ is hydrogen, or a hydrocarbon; and $R_5$ is hydrogen or methyl.

Still more preferred compounds of this invention are realized when in the above formula the hydrocarbonoxy group of $R_1$ is methoxy or ethoxy, and the hydrocarbon group of R, $R_3$ or $R_4$ is methyl or ethyl.

In addition, preferred compounds result when the R substituent is in the form of a disaccharide or an aglycone.

The instant compounds are prepared by alkylating the parent C-076 compound or the monosaccharide or aglycone derived thereof. The alkylation techniques vary depending upon the compound and the position being substituted.

All of the C-076 compounds and the monosaccharide and aglycone derivatives have a hydroxy group at the 7-position. This group is a tertiary hydroxy group and the reactions used to alkylate the other positions have no effect on this group. A reaction has been developed which is specific to this position, having no effect on the other hydroxy groups. Thus no protection of the other hydroxy groups is necessary when methylating the 7-position hydroxy.

The C-076 compound or derivatives thereof is treated with diazomethane. The reaction is carried out in a non-reactive solvent such as ether, tetrahydrofuran, glycone, and the like at from 0° C. to room temperature. The reaction is continued for from 24 to 48 hours. Substitution is exclusively at the 7-position hydroxy, however usually the product is recovered as a mixture with starting material. The separation of the product from the starting material is readily accomplished using chromatographic techniques such as column, thin layer, preparative layer or high pressure liquid chromatography. These and other techniques known to those skilled in this art will isolate the desired product in pure form.

To substitute a hydrocarbon on the other hydroxy groups present on the C-076 molecule, the appropriate starting material is treated with the hydrocarbon halide (or phenyl substituted alkyl halide) in the presence of silver oxide ($Ag_2O$) catalyst. The preferred halide employed in this process is the iodide. The halide is used in excess quantity, and the reaction is carried out at from about room temperature to 70° C. The halide may be present in a single molar excess or greater, and may even be employed as the solvent for the reaction, dispensing with the solvents listed below. The reaction is preferably carried out in a solvent such as halide reactants, ether, tetrahydrofuran, acetonitrile, methylenechlorideglyme, dichloroethane, benzene and the like. The duration of the reaction varies with the position of substitution as well as the size of the group being substituted onto the C-076 substrate. The 4", 4' and 13 positions require longer reaction times than the 5- or 23-positions and larger alkyl or substituted alkyl groups require longer reaction times. Overall, the reaction times required for this reaction is between 1 and 100 hours.

Because of the different reactivities of the various hydroxy groups, and with the use of certain protecting techniques, all possible combinations of alkylated C-076 compounds can be prepared. The hydroxy groups at the 5- and 23-positions are much more reactive to alkylation than the 4"-, 4'- or 13-positions. Thus, where the 5- or 23-alkylated compounds are desired, no protection is necessary for the 4"-, 4'- or 13-positions.

Since the 7-position hydroxy will not react except under more vigorous conditions, the C-076 A1 compounds may be readily alkylated at the 4"-, 4'-, or 13-positions (the only other way hydroxy groups present since there is no hydroxy at the 5- or 23-positions of the C-076 A1 compounds).

The C-076 A2 compounds have the 23-hydroxy group available for alkylation in addition to the 7-position and the 4"-, 4'- or 13-positions. Selective alkylation at the 7-position is carried out as described above. The 23-position may be alkylated without protection of the other hydroxy groups. If the 4"-, 4'-, or 13 alkyl compound is desired, the 23-position must be protected as described below.

The C-076 B1 compounds have the 5-position hydroxy group available for alkylation. This position may be alkylated selectively without protection of the 4"-, 4'- or 13-positions. For alkylation of the 4", 4' or 13 positions the 5-position hydroxy must be protected as described below.

The C-076 B2 compounds have both the 5 and 23 positions available for alkylation in addition to the 4", 4' or 13 positions and the 7-position. The reactivities of the 5- and 23-position hydroxy groups are about equal. If alkylation at both the 5 and 23 positions is desired, the reaction is carried out as above described. If alkylation at the 4", 4' or 13 positions is desired, protection of both of the 5 and 23 hydroxy groups is necessary. If alkylation of only one of the 5- or 23-positions is desired, the reaction is carried out as above described using minimal times and temperatures within the range given, thus resulting in a mixture of 5- and 23-substituted compounds. Such a mixture is readily separated, usually with chromatographic techniques such as column, high pressure, thin layer or preparative layer chromatography. The technique of thin layer chromatography is usually employed to follow the course of the reaction in order to maximize the formation of the individual 5- and 23-substituted compounds and to avoid the formation of the 5,23-disubstituted compounds.

The protection of the 5 and 23 positions is carried out in two ways; one applicable to the 5 and 23 positions, and the other applicable to the 5-position only.

The 5 and/or the 23 positions may be readily protected by acylating, preferably acetylating. The C-076 compound to be protected is dissolved in an aprotic, nonpolar solvent, such as one of such solvents described above, preferably ether, and an acyl halide, preferably acetyl chloride, is added dropwise, substantially at room temperature but up to a 10°–40° C. range. The reaction mixture is stirred for from 2 to 6 hours. A catalytic amount of silver oxide ($Ag_2O$) is added to the reaction. The acylated compound is isolated using known techniques.

The acyl protecting group may be removed by base catalyzed hydrolysis, such as with an alkali metal alkoxide, preferably sodium methoxide, in the corresponding alcohol, preferably methanol.

In addition, the 5-position alcohol may be oxidized to the ketone using manganese dioxide ($MnO_2$) in ether. The reaction is completed in about 10 to 30 hours at about room temperature.

The ketone is then readily converted back to the hydroxy group using borohydride reduction, preferably employing sodium borohydride in a loweralkanol, preferably methanol. The reaction is complete in about 5 minutes to 1 hour with stirring substantially at room temperature.

This oxidation-reduction reaction sequence, in combination with the acylation, is seen to aid in the preparation of C-076 B2 compounds with only one of the 5- or 23-positions alkylated. By protecting the 5-position with the 5-keto group the 23-alkyl compound is readily prepared. Or the 5-keto-23-acyl compound can be prepared, the 5-position reduced back to the hydroxy, the 5-alkyl compound prepared, and the 23-position hydrolized back to the hydroxy group.

It is noted that once a particular alkyl compound is prepared, any remaining hydroxy groups may be alkylated with the same or a different alkyl group. In this manner, derivatives with multiple and different alkyl or substituted alkyl groups may be readily prepared. In addition, the acyl compounds, which are highly active, are included within the ambit of this invention. Thus, the acyl protecting groups need not be removed at the end of a reaction sequence, any hydroxy groups which are not alkylated may then be acylated if desired. The 4"-, 4'- or 13-acyl compounds may be readily prepared following the above procedure. However, since the 4"-, 4'- and 13-positions are somewhat less reactive to acylation than the 5- or 23-positions, more vigorous reaction conditions are required. Generally, however, the reaction is complete in from 1 to 24 hours at from room temperature to 100° C.

The novel alkylated compounds of this invention have significant parasiticidal activity as anthelmintics, insecticides, ectoparasiticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, serve damage to the walls of the intestinal tract and other tissues and organs and, if left untreated, may result in death of the infected host. The alkylated C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas blowfly, in sheep *Lucilia sp.*, biting insects and such migrating dipterous larvae as *Hypoderma sp.* in cattle, Gastrophilus in horses, and *Cuterebra sp.* in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, *Blatella sp.*, clothes moth, *Tineola sp.*, carpet beetle, *Attagenus sp.* and the housefly Musca domestica.

The compounds are also useful against insect pests of stored grains such as *Tribolium sp., Tenebrio sp.* and of agricultural plants such as spider mites, (*Tetranychus sp.*), aphids, (*Acyrthiosiphon sp.*); against migratory orthopterans such as locusts and immature stages of insects living on plant tissue. The compounds are useful as a nematocide for the control of soil nematodes and plant parasites such as *Meloidogyne spp.* which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.01% by weight. The capsules and boluses comprise the active ingredient admixed with a carrier vehicle such as starch, talc, magnesium stearate, or di-calcium phosphate.

Where it is desired to administer the C-076 compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and Content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparations using solketal, glycerol-formal and aqueous parenteral formulations are also used. The active alkylated C-076 compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting and sucking insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg. per kg. of animal body weight, such total dose being given at one time or in divided doses per day. With the preferred compounds of the invention, excellent control of such parasites is obtained in animals by administering from about 0.025 to 0.5 mg. per kg. of body weight in a single dose. Repeat treatments are given as required to combat reinfections and are dependent upon the species of parasite and the husbandry techniques being employed. The techniques for administering these materials to animals are known to those skilled in the veterinary field. The compounds may also be administered in combination with other antiparasitic compounds or compounds with other biological activities to provide for a single treatment with a broadened spectrum of activity.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active alkylated C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular alkylated C-076 compound employed, the compounds of this invention are usually fed at concentrations of between 0.00001 to 0.002% in the feed in order to achieve the desired antiparasitic result.

In using the compounds of this invention, the individual alkylated C-076 components may be prepared and used in that form. Alternatively, mixtures of two or more of the individual alkylated C-076 compounds may be used as well as mixtures with other C-076 compounds and derivatives thereof.

In the isolation of the C-076 compounds, which serve as starting materials for the instant processes, from the fermentation broth, the various C-076 compounds will be found to have been prepared in unequal amounts. In particular an "a" series compound will be prepared in a higher proportion than the corresponding "b" series compound. The weight ratio of "a" series to the corresponding "b" series is about 85:15 to 99:1. The differences between the "a" series and "b" series is constant throughout the C-076 compounds and consists of a sec-butyl group and a iso-propyl group respectively at the 25 position. This difference, of course, does not interfere with any of the instant reactions. In particular, it may not be necessary to separate the "b" components from the related "a" component. Separation of these closely related compounds is generally not practiced since the "b" compound is present only in a very small percent by weight, and the structural difference has negligible effects on the reaction processes and biological activities.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that the invention might be more fully understood; they are not to be construed as limitations of the invention.

The C-076 alkyl derivatives prepared in the following examples are generally isolated as amorphous solids and not as crystalline solids. They are thus characterized analytically using techniques such as mass spectrometry, nuclear magnetic resonance and the like. Being amorphous, the compounds are not characterized by sharp melting points, however the chromatographic and analytical methods employed indicate that the compounds are pure.

EXAMPLE 1

5-O-Acetyl-4"-O-Methyl C-076 B1a and 5-O-Acetyl-4",7-Di-O-Methyl C-076 B1a

To a solution of 5-O-acetyl C-076 B1a (5 mg.) in anhydrous diethyl ether (10 ml.) is added methyliodide (10 drops) and freshly prepared silver oxide (50 mg.). The mixture is stirred in the dark under nitrogen until thin layer chromatography shows that all starting material is gone (24 hours). The solids are filtered, washed with ether, and discarded. The filtrate is evaporated under a stream of nitrogen to a residue which is resolved by preparative layer chromatography [multiple development: dichloromethane/methanol (99:1)] into two homogeneous materials, which are lyophilized from benzene. Mass spectral and 300 MHz nuclear magnetic resonance analysis confirm the structure of the products as 5-O-acetyl-4",7-di-O-methyl C-076 B1a (2 mg.) and 5-O-acetyl-5"-O-methyl C-076 B1a (2 mg.).

Deacetylation using catalytic amounts of sodium methoxide in methanol at pH of 8 to 9 affords 4"-O-methyl B1a from 5-O-acetyl-4",7-di-O-methyl C-706 B1a (greater than 80% yield). The reaction is complete in about 18 hours at room temperature.

EXAMPLE 2

5-O-Ethyl C-076 B1a and 4",5-Di-O-Ethyl C-076 B1a

To C-076 B1a (50 mg.) in anhydrous diethyl ether (25 ml.) is added ethyl iodide (1 ml.) and freshly prepared silver oxide (250 mg.). The mixture is stirred in the dark under nitrogen for four days (until starting material is gone as determined by thin layer chromatography). The solids are filtered, washed with ether, and discarded. The filtrate is evaporated to dryness under a stream of nitrogen and resolved into two major components by preparative layer chromatography [multiple development, benzene/2-propanol (19:1)]. The colorless solids (after lyophilization from benzene) are confirmed by mass spectral and 300 MHz nuclear magnetic resonance analysis to be 4",5-di-O-ethyl C-076 B1a (9 mg.) and 5-O-ethyl C-076 B1a (32 mg.).

EXAMPLE 3

7-O-Methyl C-076 B1a

To a solution of C-076 B1a (50 mg.) in anhydrous diethyl ether (50 ml.) is added an ethereal solution of diazomethane (3–4 mmoles, prepared from nitrosomethylurea by the original synthesis procedure, and dried over potassium hydroxide pellets). The stoppered vessel is stored at room temperature for four days until no further reaction takes place as determined (by thin layer chromatography). Nitrogen is bubbled through the solution to remove any excess diazomethane and the solvent. The residue is resolved into two bands by preparative layer chromatography [multiple development, benzene/2-propanol (19:1)] which are lyophilized from benzene and identified by mass spectral and 300 MHz nuclear magnetic resonance analysis as C-076 B1a (40 mg., starting material) and 7-O-methyl-C-076 B1a (7 mg.).

EXAMPLE 4

5-O-n-Heptyl-C-076-B1a and 4″-O-n-Heptyl-C-076-B1a

To n-heptyl iodide (100 mg.) in anhydrous diethyl ether (25 ml.) is added freshly prepared silver oxide (210 mg.) and C-076 B1a (25 mg.). The mixture is stirred under nitrogen for two days, when by thin layer chromatography the reaction appears to have stopped. The solids are filtered, washed with fresh ether and discarded. The filtrate is evaporated under nitrogen to a residue which is chromatographed by preparative chromatography [dichloromethane/methanol (49:1)] into three major bands. Resolution of the bands is complicated by the presence of unreacted n-heptyl iodide and heptanol. Each of the bands is repurified to homogeneity by multiple development preparative layer chromatography using benzene/2-propanol (19:1) as developer, and lyophilized from benzene to afford 5-O-n-heptyl C-076 B1a (10 mg.), 4″-O-n-heptyl-C-076 B1a (3 mg.) and C-076 b1a (4 mg., unreacted starting material) as colorless solids. Mass spectral and 300 MHz nuclear magnetic resonance data are consistent with the proposed structures.

EXAMPLE 5 4″-O-Methyl C-076 A2a and 4″,23-Di-O-Methyl-C-076 A2a

To a solution of C-076 A2a (10 mg.) in anhydrous diethyl ether is added freshly prepared silver oxide (50 mg.) and methyl iodide (6 drops). The stoppered flask is stirred in the dark under nitrogen for two days at which time thin layer chromatography shows that starting material is gone. The solids are filtered, washed with fresh solvent, and discarded. The filtrate is evaporated under a stream of nitrogen and resolved by preparative layer chromatography [benzene/2-propanol (39:1), multiple development] into two homogeneous materials. Mass spectral and 300 MHz nuclear magnetic resonance analysis showed the products to be 4″-O-methyl C-076 A2a (5 mg.) and 4″,23-di-O-methyl C-076 A2a (4 mg.).

EXAMPLE 6

23-O-Methyl C-076 A2a Aglycone, 13-O-Methyl C-076 A2a Aglycone and 13,23-Di-O-Methyl C-076 A2a Aglycone To a solution of C-076 A2a aglycone (10 mg.) in anhydrous diethyl ether (5 ml.) is added freshly prepared silver oxide (50 mg.) and methyl iodide (0.25 ml.). The mixture is stirred in the dark under nitrogen for three days, when thin layer chromatography shows no further reaction progress. The solids are filtered, washed with fresh solvent, and discarded. The combined filtrate and washings are evaporated under a stream of nitrogen and resolved into four components by preparative layer chromatography [benzene/2-propanol (99:1), multiple development]. The products are identified by mass spectral and nuclear magnetic resonance analysis as 23-O-methyl C-076 A2a aglycone (7 mg.), 13-O-methyl C-076 A2a aglycone (1 mg.), 13,23-di-O-methyl C-076 A2a aglycone (1 mg.) and recovered starting material (2 mg.).

EXAMPLE 7

4″-O-Methyl C-076 A1a, 4″,7-Di-O-Methyl C-076 A1a, and 4″-O-Methyl C-076 B1a To a solution of C-076 B1a (50 mg.) in anhydrous diethyl ether (20 ml.) is added freshly prepared silver oxide (250 mg.) and methyl iodide 1.0 ml.). The stoppered flask is stirred in the dark under nitrogen until starting material has disappeared as observed by thin layer chromatography (2 days). The solids are filtered, washed with fresh solvent, and discarded. The filtrate is evaporated under a stream of nitrogen to a residue which is fractionated by preparative layer chromatography [benzene/2-propanol (39:1), multiple development] or by high pressure liquid chromatography on $C_{18}$ Bondapak using methanol/water (85:15) into three components: 4″,5-di-O-methyl C-076 B1a (25 mg., 4″-O-methyl C-076 A1a),4″,5,7tri-O-methyl C-076 B1a (4 mg, 4″,7-di-O-methyl C-076 A1a) and 5 -O-methyl C-076 B1a (3 mg., C-076 A1a). Structures are confirmed by mass spectral and nuclear magnetic resonance data.

Repetition of the experiment with shorter time periods (24 hours) and less methyl iodide (0.2 to 0.4 ml.) results in the nearly exclusive preparation of 5-O-methyl C-076 B1a (C-076 A1a).

EXAMPLE 8

5-O-Benzyl C-076 B1a and 4″,5-Di-O-Benzyl C-076 B1a

To a solution of C-076 B1a (35 mg.) in anhydrous diethyl ether (20 ml.) is added benzyl bromide (0.5 ml.) and freshly prepared silver oxide (150 mg.). After stirring the reaction mixture in the dark under nitrogen for two days, the solids are filtered, washed with fresh solvent, and discarded. The filtrate is evaporated under a stream of nitrogen and the residue resolved by preparative layer chromatographyl [benzene/2-propanol (19:1), multiple development]. The two major products are isolated as chromatographically homogeneous lyophilized solids identified by spectral analysis as 5-O-benzyl C-076 B1a (10 mg.) and 4″,5-di-O-benzyl C-076 B1a (11 mg.).

EXAMPLE 9

4′-O-Heptyl C-076 B1a monosaccharide, 5-O-Heptyl C-076 B1a Monosaccharide, and 4′,5-Di-O-Heptyl C-076 B1a Monosaccharide To a solution of C-076 B1a monosaccharide (15 mg.) in anhydrous diethyl ether (50 ml.) is added n-heptyl iodide (0.5 ml.) and freshly prepared silver oxide (400 mg.). The progress of the reaction, stirred in the dark under nitrogen, is monitored by thin layer chromatography. After four days, no further progress is made and the solids are filtered, washed with solvent, and discarded. The solvent is evaporated under a stream of nitrogen and the residue resolved into four major bands on preparative layer chromatography[benzene/2-propanol (19:1), multiple development]. Spectral analysis shows the products to be 4',5-di-O-heptyl C-076 B1a monosaccharide (3 mg.), 5-O-heptyl C-076 B1a monosaccharide (6 mg.), 4'-O-heptyl C-076 B1a monosaccharide (3 mg.) and starting material (3 mg.).

EXAMPLE 10

5-O-Acetyl C-076 B1a (intermediate for Example 1)

To a solution of C-076 B1a (100 mg.) in anhydrous diethyl ether (50 ml.) is added freshly prepared silver oxide (400 mg.) and ethereal acetyl chloride (aliquots containing 50 mg.) Every 30 minutes thin layer chromatography (benzene/2-propanol [19:1]) shows the initial formation of a slightly faster spot (5-O-acetyl C-076 B1a) and aliquots of acetyl chloride (total of 8) are added to maximize formation of this spot. After approximately one hour a second faster spot (diacetate) began forming slowly. The solids are filtered, washed with fresh solvent, and discarded. The filtrate is evaporated under a stream of nitrogen and the monoacetyl derivative isolated by purification on preparative layer chromatography [chloroform followed by chloroform/methanol (199:1), multiple development]. The homogeneous product is lyophilized from benzene (45 mg.).

EXAMPLE 11

4"-O-Methyl C-076 B1a

C-076 B1a (50 mg.) is dissolved in anhydrous diethyl ether (50 ml.) and active manganese dioxide (100 mg.) added. The reaction mixture is stirred for 18 hours before the solids are filtered, washed with fresh solvent, and discarded. The filtrate, containing homogeneous C-076 B1a-5-one is reduced to approximately the original volume before methyl iodide (0.5 ml.) and freshly prepared silver oxide (150 mg.) are added. When the reaction (mixture was stirred in the dark under nitrogen) is judged to be complete by thin layer chromatography, the solids are filtered, washed, and discarded. The filtrate is evaporated under reduced pressure and the residue dissolved in methanol (25 ml.) and sodium borohydride (50 mg.) is added. After 30 minutes, 5 ml. of acetone is added and the mixture evaporated to a residue. Chromatographic resolution of the product [preparative layer chromatography on dichloromethane/methanol (49:1), multiple development] affords after lyophilization from benzene a colorless solid (18 mg.), which is identical in all respects to a product prepared by deacylation of 5-O-acetyl-4"-O-methyl C-076 B1a (see Example 1).

PREPARATION 1

A 250 ml. baffled Erlenmeyer flask containing 50 ml. of the following medium:

| | |
|---|---|
| Lactose | 2.0% |
| Distiller's solubles | 1.5% |
| Autolyzed yeast, Ardamine pH | 0.5% |
| pH - before sterilization | 7.0 | is inoculated with the contents of one frozen vial of *Streptomyces avermitilis* MA 4848 and incubated on a rotary shaker at 28° C. for 24 hours at 150 RPM.

10 Ml. of the above fermentation media is employed to inoculate 500 ml. of the same medium as above in a 2 liter baffled Erlenmeyer flask. The fermentation media is incubated at 150 RPM on a rotary shaker at 28° C. for 24 hours.

All of the foregoing media is employed to inoculate 467 liters of the following media in a 756 liter stainless steel fermentor:

| | |
|---|---|
| Lactose | 2.0% |
| Distiller's solubles | 1.5% |
| Autolyzed yeast, Ardamine pH | 0.5% |
| Polyglycol 2000 | 0.32 ml./liter |
| pH - before sterilization | 7.0 |

The fermentation media is incubated at 28° C. for 40 hours with an air flow 10 cubic feet per minute and an agitation rate 130 RPM.

230 Liters of the above media is employed to inoculate 4,310 liters of the following medium in a 5,670 liter stainless steel fermentor:

| | |
|---|---|
| Dextrose | 4.5% |
| Peptonized milk | 2.4% |
| Autolyzed yeast, Ardamine pH | 0.25% |
| Polyglycol 2000 | 2.5 ml./liter |
| pH - before sterilization | 7.0 |

The fermentation continues for 144 hours at 26° C. with an air flow rate of 54.3 cubic feet per minute and agitation of 120 RPM.

The fermentation media are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 2000 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

PREPARATION 2

The 60 liter solution of C-076 in methylene chloride of the previous example is concentrated to dryness in vacuo and the residue is combined 3 times with 60 liter portions of methanol and evaporated to dryness to remove any residual methylene chloride. The final methanol concentrate volume is approximately 36 liters. The methanol solution is stored overnight and filtered. The filter cake is washed with 40 liters of fresh methanol and the methanol filtrates and washings are combined. The methanol solution is combined with 95 liters of ethylene glycol and 130 liters of heptane. The 2 layer solution is agitated for 5 minutes and the lower layer (ethylene glycol and methanol) is separated. The heptane solution is washed with a mixture of 20 liters of ethylene glycol and 6.3 liters methanol. After five minutes of agitation, the lower layer is separated and combined with the first ethylene glycol/methanol extract. An equal volume of water (approximately 150 liters) containing 79 g. of salt per liter is added to the ethylene glycol/methanol extracts. This solution is extracted with 150 liters of ethyl ether with agitation for 5 minutes. The ether layer is washed with 75 liters of water (½ volume) and agitated for 5 minutes and the layers separated. This procedure is repeated an additional 2 times (the final water wash contains 20 g. of salt per liter) affording a final ether layer volume of 110 liters. The ether layer is concentrated in vacuo, to a minimum volume, keeping the temperature less than 25° C. 40 Liters of methylene chloride is added to the residue and the solution is evaporated to dryness. This procedure is repeated and the final residue concentrated in vacuo at 50° C. to dryness.

PREPARATION 3

A 30 centimeter diameter column is prepared with a layer of 34 kilograms of activated alumina followed by a layer of 34 kilograms of activated carbon in a solution of methylene chloride. The residue from the previous example is dissolved in methylene chloride to a volume of 34 liters and applied to the column and eluted with 34 liters of methylene chloride. these fractions are discarded. A 3% solution of isopropanol and methylene chloride (20.8 liters of isopropanol and 660 liters of methylene chloride) is applied to the column and eluted in approximately 200 liter fractions. The combined isopropanol and methylene chloride fractions are evaporated in vacuo at a bath temperature of about 60° C. to a volume of about 20 liters. The bath temperature is reduced to about 45° C. and the extract is evaporated to dryness in vacuo. The residue is dissolved in 10 parts methylene chloride, 10 parts hexane and one part methanol to a final volume of 15 liters. This solution is applied directly to the Sephadex LH-20 column of the next example.

PREPARATION 4

A 30 centimeter diameter column is prepared in methanol with 36 kilograms of Sephadex LH-20 (available from Pharmacia Fine Chemicals, 800 Centennial Avenue, Piscataway, New Jersey 08854) and washed with a solvent consisting of 10 parts methylene chloride, 10 parts hexane and one part methanol. One-fourth of the C-076 solution of Example 10 is applied to the column and the column eluted at a rate of 250 ml. per minute. Two 20 liter forecuts are collected and discarded followed by 20 two liter rich cuts (identified as fractions 1–20), followed by a single 20 liter tail cut, which is discarded. Fractions 1–8 are found to contain the C-076 A compounds and fractions 9–20 are found to contain the C-076 B compounds.

PREPARATION 5

The process of Preparation 4 is repeated on the same scale three more times and all of the fractions containing the C-076 B components (fractions 9–20) are combined and evaporated to dryness, affording 818 g. of crude mixed C-076 B components. The sample is found to contain 55% C-076 B1 and 39% of C-076 B2. 680.5 G. of this sample is dissolved in 2 liters of methylene chloride and placed in a 22 liter three neck round bottom flask followed by the addition of 13.6 liters of methanol. The methylene chloride is removed by distillation. 13.6 Liters of ethylene glycol is added as the methanol is being distilled under reduced pressure. The rate of distillation is maintained such that the temperature of the solution did not go below 65° C. When the addition of the ethylene glycol is complete, the solution is allowed to cool at 5° C. for sixteen hours. The crystals are filtered and washed with 1 liter of cold ethylene glycol. The crystals are then redissolved in 2 liters of methylene chloride the solution placed in a 22 liter three necked round bottom flask. The procedure described above is repeated twice. The first time 12.5 liters each of methanol and ethylene glycol is employed and the second time 13.6 liters each of methanol and ethylene glycol is employed. The final crystals are washed with 1 liter of cold ethylene glycol and 1 liter of water. The crystals are dissolved in 4 liters of water and dried by filtering through sodium sulfate. The benzene solution is concentrated to a volume of 2 liters and lyophilized affording 241.2 gm. of a white powder consisting of 98% C-076 $B_1$ and 1% of C-076 $B_2$.

The mother liquors (22 liters) from the first two crystallizations above are combined and diluted with 22 liters of water. The aqueous solution is extracted with 60 liters of toluene and again with 15 liters of toluene. The toluene extract is then washed with 48 liters of water. The organic phase is filtered through Super-Cel to remove any residual water and evaporated affording 336 gm. of solid material consisting of 79% C-076 $B_2$ and 16% C-076 $B_1$ compounds.

PREPARATION 6

In the four Sephadex LH-20 columns of the procedure of Preparation 4, fractions 1–8 contain the C-076 A compounds and are combined. By HPLC analysis the mixture is found to contain 252 g. of C-076 A2a, 16 g. of A2b, 94 g. of A1a and 24 g. of A1b. The material is dissolved in a solvent system consisting of hexane:toluene:methanol in the proportion of 6:1:1 and applied to the Sephadex LH-20 column of the same dimensions as the one used in Preparation 4 in the above solvent. Fractions are collected at the rate of 250 ml. per minute and a 20 liter forecut is collected and discarded. Further elution affords 2 additional 20 liter forecuts which are also discarded and 50 four liter rich cuts and which contain C-076 A compounds. Fractions 3–8 are found to contain predominately C-076 A1 components (40.2 g. A1a and 6.7 g. A1b), and fractions 29–36 are found to contain C-076 A2 compounds (117.2 g. A2a and 7.35 g. of A2b). Fractions 9–28 contain a mixture of C-076 A1 and A2 compounds.

PREPARATION 7

A sample of 150 g. of C-076 B1 from Preparation 5 is dissolved in 3 liters of a solvent mixture of hexane:toluene:methanol in the ratio of 3:1:1. The solution is passed through a column of Sephadex LH-20 (of the same dimensions as the one used in Preparation 4) in the above solvent taking fractions at the rate of 250 ml. per minutes. After two 20 liter portions of the solvent mixture are collected and discarded, forecut of 10 liters is taken and discarded. Then 30 richcuts of 2 liters each are taken. Fractions 1–13 and 25–30 are discarded. Fractions 14–16 are combined and contain 80 g. of predominately C-076 B1a. Fractions 22–24 are combined and contain 6.7 g. of predominately C-076 B1b. Fractions 17–21 contain a mixture of C-076 B1a and B1b.

Fractions 17–21 above are combined and concentrated and passed through a Sephadex LH-20 column with the same solvent system as above. Three 20 liter forecuts are taken and discarded. Richcuts are then taken as follows: 5 cuts of 2 liters each (fractions 1–5); 20 cuts of 1 liter each (fractions 6–25); and 10 cuts of 2 liters each (fractions 26–35). Fractions 1–15 are discarded; fractions 16–21 contain 13.5 g. of C-076 B1a and 0.4 g. of C-076 B1b; fractions 22–26 contain 44 g. of C-076 B1a and 0.13 g. of C-076 B1b; fractions 27–30 contain 10.2 g. of C-076 B1a and 0.8 g. of C-076 B1b.

PREPARATION 8

A mixture of all 8 C-076 components are chromatographed on a high pressure liquid chromatography column 4 mm.×30 cm. packed with 10 micron$\mu$ Bondapak $C_{18}$ silica gel (available from Waters Associates Inc., Maple Street, Milford, Massachusetts 01757) eluting with 85:15 (v/v) methanol:water at a constant 40° C. At a flow rate of 1.2 ml. per minute all eight compounds are separated and the elution volumes, which under the foregoing constant conditions are characteristic of the individual compounds are as follows:

|  | Elution Volume (Ve) Ml |
|---|---|
| C-076 $B_2b$ | 5.90 |
| C-076 $B_2a$ | 6.52 |
| C-076 $A_2b$ | 7.12 |
| C-076 $A_2a$ | 7.88 |
| C-076 $B_1b$ | 8.36 |
| C-076 $B_1a$ | 9.60 |
| C-076 $A_1b$ | 10.24 |
| C-076 $A_1a$ | 11.88 |

The separation of C-076 "b" components from the respective "a" components is accomplished using techniques such as high pressure liquid chromatography. An absolute methanol solution of 30 microliters of a mixture of C-076 A1a and A1b, estimated to contain 30 micrograms of C-076 A1b is placed on a 3×250 mm. high pressure liquid chromatography column containing Spherisorb 5 micron ODS (available from Spectra Physics) as packing. The column is eluted with 85:15 methanol-water at a rate of 0.15 ml./min. The elution of the products are followed by observing the ultraviolet absorption of the eluent and collecting the individual components at the outlet of the UV monitor. 30 Micrograms of C-076 A1b is recovered in this manner.

What is claimed is:

1. A compound having the formula:

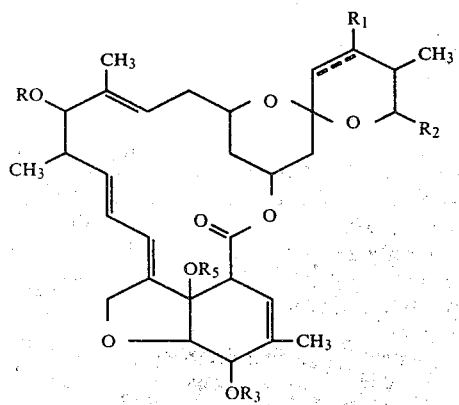

wherein the broken line indicates a single or double bond;

$R_1$ is hydroxy, loweralkanoyloxy or a hydrocarbonoxy and is present only when the broken line indicates a single bond;

$R_2$ is iso-propyl or sec-butyl;

$R_3$ is hydrogen, methyl, loweralkanoyl or a hydrocarbon; and

R is hydrogen, loweralkanoyl, a hydrocarbon, or

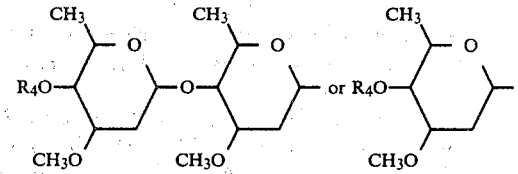

wherein $R_4$ is hydrogen, loweralkanoyl or a hydrocarbon;

$R_5$ is hydrogen or methyl; and said hydrocarbonoxy group of $R_1$ is an alkoxy of from 1 to 10 carbon atoms or an alkoxy of from 1 to 10 carbon atoms substituted with phenyl and said hydrocarbon group in R, $R_1$, and $R_4$ is an alkyl of from 1 to 10 carbon atoms or an alkyl of from 1 to 10 carbon atoms substituted by phenyl; and said hydrocarbon group in $R_3$ is an alkyl of from 1 to 10 carbon atoms substituted by phenyl provided that at least one of the R, $R_1$, $R_3$, or $R_4$ is or contains a hydrocarbon or $R_5$ is methyl.

2. A compounds of claim 1 wherein the broken line indicates a single or a double bond;

$R_1$ is hydroxy or hydrocarbonoxy and is present only when the broken line indicates a single bond;

$R_2$ is iso-propyl or sec-butyl;

$R_3$ is hydrogen, methyl or a hydrocarbon;

R is hydrogen, a hydrocarbon or

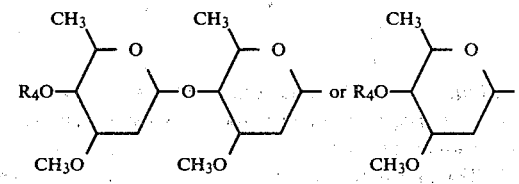

wherein $R_4$ is hydrogen or a hydrocarbon; and $R_5$ is hydrogen or methyl.

3. A compound of claim 2 wherein the hydrocarbonoxy group of $R_1$ is methoxy or ethoxy, and the hydrocarbon group of R, $R_3$ and $R_4$ is methyl or ethyl.

4. The compound of claim 2 wherein $R_2$ is iso-propyl.

5. The compound of claim 2 wherein $R_2$ is sec-butyl.

6. The compound of claim 5 wherein R is hydrogen, methyl, ethyl or

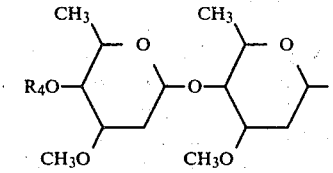

wherein $R_4$ is hydrogen, methyl or ethyl.

7. The compound of claim 6 wherein R is 5 hydrogen, methyl or said disaccharide wherein $R_4$ is hydrogen or methyl.

8. A compound of claim 7 wherein R is:

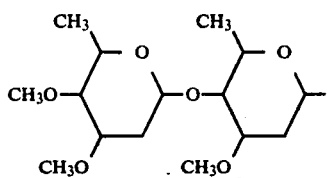

$R_1$ and the broken line indicate a 22, 23 double bond, $R_2$ is sec-butyl, $R_3$ is hydrogen and $R_5$ is hydrogen which is 4"-O-methyl C-076 B1a.

9. The compound of claim 7 wherein R is methyl, $R_1$ and the broken line indicates a 22, 23 double bond, $R_2$ is sec-butyl, $R_3$ is hydrogen and $R_5$ is hydrogen which is 13-O-methyl C-076 B1a aglycone.

10. The compound of claim 7 wherein R is:

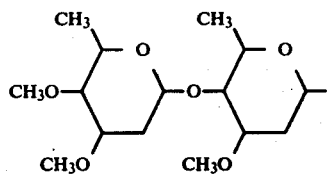

$R_1$ and the broken line indicates a 22, 23 double bond, $R_2$ is sec-butyl, $R_3$ is acetyl and $R_5$ is hydrogen, which is 5-O-acetyl-4"-O-methyl C-076 B1a.

11. The compound of claim 7 wherein R is:

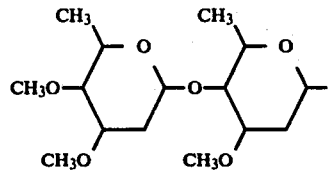

$R_1$ is hydroxy, the broken line indicates a single bond, $R_2$ is sec-butyl, $R_3$ is methyl and $R_5$ is hydrogen which is 4"-O-methyl C-076 A2a.

12. The compound of claim 7 wherein R is:

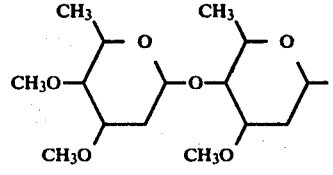

$R_1$ is methoxy, the broken line indicates a single bond, $R_2$ is sec-butyl, $R_3$ is methyl and $R_5$ is hydrogen which is 4",23-di-O-methyl C-076 A2a.

13. The compound of claim 7 wherein R is methyl, $R_1$ is hydroxy, the broken line indicates a single bond, $R_2$ is sec-butyl, $R_3$ is methyl, and $R_5$ is hydrogen which is 13-O-methyl C-076 A2a aglycone.

14. The compound of claim 7 wherein R is methyl, $R_1$ is methoxy, the broken line indicates a single bond, $R_2$ is sec-butyl, $R_3$ is methyl, and $R_5$ is hydrogen, which is 13,23-di-O-methyl C-076 A2a aglycone.

15. The compound of claim 7 wherein R is:

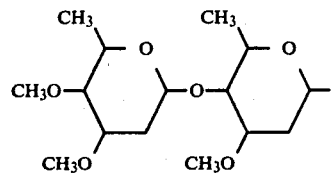

$R_1$ and the broken line indicates a 22, 23 double bond, $R_2$ is sec-butyl, $R_3$ is methyl, and $R_5$ is hydrogen which is 4"-O-methyl C-076 A1a.

16. The compound of claim 5 wherein $R_1$ is 10 methoxy or ethoxy.

17. The compound of claim 16 wherein R is:

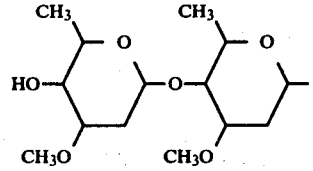

$R_1$ is methoxy, the broken line indicates a single bond, $R_2$ is sec-butyl, $R_3$ is methyl and $R_5$ is hydrogen, which is 23-O-methyl C-076 A2a.

18. The compound of claim 16 wherein R is hydrogen, $R_1$ is methoxy, $R_2$ is sec-butyl, $R_3$ is methyl, and $R_5$ is hydrogen which is 23-O-methyl C-076 A2a aglycone.

19. The compound of claim 5 wherein said broken line indicates a double bond.

20. The compound of claim 5 wherein $R_3$ is ethyl.

21. The compound of claim 20 wherein R is

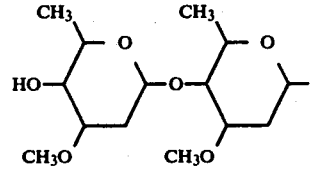

$R_1$ is hydroxy, the broken line indicates a single bond, $R_2$ is sec-butyl, $R_3$ is ethyl and $R_5$ is hydrogen which is 5-O-ethyl C-076 B2a.

22. The compound of claim 20 wherein R is:

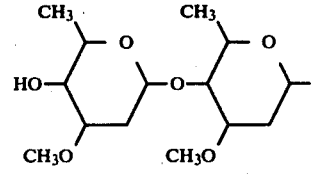

$R_1$ and the broken line indicates a 22, 23 double bond, $R_2$ is sec-butyl, $R_3$ is ethyl and $R_5$ is hydrogen which is 5-O-ethyl C-076 B1a.

23. A method for the treatment of parasitic infections which comprises administering to a host infected with parasitic infections, an effective amount of a compound of claim 1.

24. A composition useful for the treatment of parasitic infections which comprises an inert carrier and a compound of claim 1.

* * * * *